US010792445B2

United States Patent
Krueger et al.

(10) Patent No.: US 10,792,445 B2
(45) Date of Patent: Oct. 6, 2020

(54) SPACER CHAMBER COMPRISING AN OPERATING MEANS FOR AN INHALER

(71) Applicant: Pari GmbH Spezialisten fuer effektive Inhalation, Starnberg (DE)

(72) Inventors: Ulf Krueger, Munich (DE); Emir Jelovac, Munich (DE); Birgit Lohre, Munich (DE)

(73) Assignee: Pari GmbH Spezialisten fuer effektive Inhalation, Starnberg (DE)

( * ) Notice: Subject to any disclaimer, the term of this patent is extended or adjusted under 35 U.S.C. 154(b) by 980 days.

(21) Appl. No.: 14/804,560

(22) Filed: Jul. 21, 2015

(65) Prior Publication Data

US 2016/0030688 A1 Feb. 4, 2016

(30) Foreign Application Priority Data

Jul. 29, 2014 (DE) .................. 10 2014 011 271

(51) Int. Cl.
*A61M 15/00* (2006.01)

(52) U.S. Cl.
CPC ...... *A61M 15/0086* (2013.01); *A61M 15/009* (2013.01); *A61M 15/0021* (2014.02); *A61M 15/0065* (2013.01)

(58) Field of Classification Search
CPC ............ A61M 15/0086; A61M 15/009; A61M 15/0021; A61M 15/0065; G01N 27/02; G01N 27/026; G01N 27/028; G01N 27/045; G01N 27/07; G01N 27/223; G01N 27/048
USPC ........................................ 128/200.18, 200.23
See application file for complete search history.

(56) References Cited

U.S. PATENT DOCUMENTS

| | | | |
|---|---|---|---|
| 3,405,843 A | 10/1968 | Watson, Jr. | |
| 4,592,348 A | 6/1986 | Waters et al. | |
| 6,453,900 B1 | 9/2002 | Barnes, Jr. et al. | |
| 7,562,656 B2 | 7/2009 | Gallem et al. | |
| 8,659,589 B2 | 2/2014 | Lawrence et al. | |
| 8,695,589 B2 | 4/2014 | Mullane et al. | |
| 2002/0157664 A1 | 10/2002 | Fugelsang et al. | |
| 2004/0055596 A1* | 3/2004 | Bacon ................. | A61M 15/009 128/200.23 |
| 2006/0076011 A1* | 4/2006 | Rasor .................... | A61H 33/14 128/200.24 |

(Continued)

FOREIGN PATENT DOCUMENTS

| | | |
|---|---|---|
| EP | 1358901 A2 | 11/2003 |
| EP | 2008678 A2 | 12/2008 |

(Continued)

*Primary Examiner* — Victoria Murphy
(74) *Attorney, Agent, or Firm* — Murphy, Bilak & Homiller, PLLC

(57) ABSTRACT

A spacer chamber for an inhaler includes a housing chamber, a mouthpiece arranged on a side of the housing chamber, and a connecting means arranged on the housing chamber opposite to the mouthpiece to connect the inhaler. A lever means is held on the housing chamber which is movable to two positions and has an active surface that is arranged in such a manner that the active surface can act on an activation element of the inhaler in any one of the positions, if the inhaler is connected to the connecting means. The lever means includes a lever element and a lever carrier for carrying the lever element, which is fastened to the housing chamber.

14 Claims, 9 Drawing Sheets

(56) References Cited

U.S. PATENT DOCUMENTS

2007/0074718 A1*  4/2007  Austin .............. A61M 15/0086
                                                128/200.23
2012/0103326 A1*  5/2012  Karle ....................... A61D 7/04
                                                128/200.21

FOREIGN PATENT DOCUMENTS

WO      2007041669 A2    4/2007
WO    WO-2009052563 A1 *  4/2009  ............... A61D 7/04

\* cited by examiner

SPACER CHAMBER COMPRISING AN OPERATING MEANS FOR AN INHALER

PRIORITY CLAIM

This application claims priority to German Patent Application No. 10 2014 011 271.3 filed on 29 Jul. 2014, the content of said application incorporated herein by reference in its entirety.

TECHNICAL FIELD

The invention relates to a spacer chamber comprising an operating means for an inhaler.

BACKGROUND

For the treatment of patients with respiratory diseases it is known to supply medicinal products in the form of an aerosol to patients. The aerosol is frequently supplied with the aid of an inhaler (also referred to as an MDI—metered-dose inhaler).

Such an inhaler includes a container accommodating the medicinal product in liquid form. A dosage means leading to a mouth element, which can be taken by the operator into his/her mouth in the case of application, is arranged at the outlet of the container accommodated in a holder. Application is effected frequently by the operator by pressing on the bottom of the inhaler, whereby a predetermined amount of the medicinal product is made available as an aerosol in the form of a puff via the dosage means. The mouth element forms an integral unit with the holder usually consisting of plastic. The dosage means is mounted on the container.

Any intended absorption of the medicinal product requires from the patient to press on the activation element and/or the container of the inhaler at the same time and breathe in the aerosol via the mouth at the same time. This coordination of two processes at the same time can overstrain very sick patients, but also children or the elderly. Thus, it is possible that the aerosol dosage is introduced into the patient's oral cavity via the mouthpiece only, but is not inhaled into the airways. The medicinal product drops in the aerosol then adhere to the oral mucosa and cannot fulfil their predetermined effect.

For this purpose, spacer chambers have been developed, which can be inserted between the mouth element of the inhaler and the patient's mouth.

A spacer chamber includes a housing chamber and/or a cavity on which a connecting means is provided to which an inhaler not belonging to the spacer chamber can be attached. Furthermore, a mouthpiece is available for the patient on the cavity. The patient or a helper can then first of all operate the inhaler, whereby the medicinal product aerosol enters the spacer chamber. In a separate, chronologically subsequent step, the patient can then breathe in the aerosol via the mouthpiece.

Thus, inhalation can be chronologically equalized with the aid of such a spacer chamber. It is no longer required to operate the inhaler and breathe in at the same time. Rather, the inhaler can first of all be operated to produce the aerosol and only then, under circumstances a few seconds later, the aerosol can be breathed in.

Such a spacer chamber is known from U.S. Pat. No. 7,562,656 B2.

Although spacer chambers have proved themselves very well in practice, it has been found that, due to the size of the spacer chambers, their operation usually requires two hands. For example, the spacer chamber must be held with one hand, while the inhaler is activated with the other hand. Especially for babies this can be problematic, since the parents must hold the child with at least one hand, so that only one free hand is available with which the spacer chamber must then be held to the child's mouth and the inhaler activated at the same time.

For this purpose, spacer chambers have been developed where the inhaler can each been activated with the aid of levers. Such spacer chambers and/or arrays of spacer chambers and inhalers are, for example, described in U.S. Pat. Nos. 8,695,589 B2, 6,453,900 B1, and US 2007/0074718 A1.

The well-known devices are constructed in a relatively complex manner and require a complete new development of the spacer chamber in each case. In addition, the inhalers cannot be used in the standard sales appearance, i.e. with mouthpiece.

SUMMARY

The invention is based on the object to provide a spacer chamber for an inhaler which is constructed in a simple manner, and where the inhaler can be inserted complete in a ready-to-use state.

The object is solved by the spacer chamber described in accordance with the embodiments described herein. Furthermore, an inhalation device comprising the spacer chamber and an inhaler is also provided.

A spacer chamber for an inhaler according to the invention includes a housing chamber as well as a mouthpiece arranged on the housing chamber, a connecting means arranged on the housing chamber to connect the inhaler, and an operating means held on the housing chamber. The operating means is movable to two positions and includes an active surface which is arranged in such a manner that the active surface can act on an activation element of the inhaler in any one of the positions of the operating means, if the inhaler is connected to the connecting means.

The mouthpiece can be provided on one side of the housing chamber, while the connecting means can be arranged remote from the mouthpiece, e.g. opposite to the mouthpiece, on the housing chamber. If the housing chamber has an essentially cylindrical, tubular form, the mouthpiece can then be provided on one front side and the connecting means on the opposite front side.

The housing chamber serves as a chamber in which the aerosol coming from the inhaler can be "stored intermediately", before the patient sucks it in via the mouthpiece. The inhaler, in turn, can—with its mouthpiece—be fastened to the connecting means which is arranged on the housing chamber, e.g. opposite to the mouthpiece.

In this regard, the construction of the spacer chamber corresponds to the construction as known from U.S. Pat. No. 7,562,656 B2.

In addition, the operating means is provided which is movable to two positions. In the first position, the active surface can press on the activation element of the inhaler and thus activate a puff. In the second position, the active surface does not press on the activation element, so that the device is in a state of rest.

The spacer chamber is defined without an inhaler to provide the possibility of inserting and/or fastening the inhaler into the connecting means only if required. If the inhaler is in its intended position inside the connecting means, the active surface provided on the operating means is opposite to the activation element. The activation element can, for example, be the bottom of the inhaler container which is usually pressed by a patient with his/her fingers, if he/she operates the inhaler directly.

The operating means is held directly on the housing chamber. Thus, the possibility exists to retrofit the operating means also subsequently for a spacer chamber already available according to U.S. Pat. No. 7,562,656 B2. Further modifications on the spacer chamber known from the prior art are not necessary in this case.

The connecting means can be shaped annular, releasably fastened and formed on the housing chamber to releasably carry the inhaler. In doing so, it is particularly practical, if the housing chamber has a cylindrical, tubular basic form. The connecting means can then be inserted into and/or clamped onto the front side, opposite to the mouthpiece.

The operating means can include a lever means, with the lever means able to include a lever element and a lever carrier carrying the lever element, and the lever element is movable, in particular swivelable, relative to the lever carrier. The movability of the lever element relative to the lever carrier can also be effected in the form of a linear movement. In addition, the lever element is slidable relative to the lever carrier.

In doing so, the lever carrier can be fastened, in particular, releasably fastened, to the housing chamber. The fastening can, for example, be to the housing chamber in the vicinity of the mouthpiece, so that the lever element extends away from the mouthpiece and the lever carrier along the middle axis of the housing chamber to the opposite connecting means and thus the inhaler.

Thus, the lever carrier carries the lever element, which predominantly has a longitudinal extension, on the housing chamber. The lever carrier can be fastened permanently or releasably to the housing chamber. For example, the lever carrier can be fastened to the housing chamber by clicking on, snapping on, or by a plug connection, a bolted connection, an adhesive bond or a tilt connection on the housing chamber and/or outside wall of the housing chamber.

For this purpose, the housing chamber need not have any particular mechanism. Rather, the lever carrier can also be fastened to a housing chamber of a spacer chamber already known from the prior art, without modifications being required thereof.

To achieve swivelability of the lever element relative to the lever carrier it is possible to design the lever element in a spring elastic manner. Similarly, also the lever carrier can be elastic, with the lever, in turn, then able to be designed in a rigid manner as well, if the elasticity and/or movability of the lever carrier are sufficient.

Additionally or alternatively, a hinge means can be arranged between the lever element and the lever carrier, with the lever element being swivelable relative to the lever carrier due to the hinge means. The hinge means thus effects a rotatory degree of freedom for the lever element. In addition, spring elastic elasticity of the lever element is possible.

The hinge means can provide a rotation axis as the hinge. It can also be realized as a film hinge, for example.

In one embodiment the lever element can have an elongated extension and be held on the level carrier on a carrier-sided end. The active surface can be formed on the other inhaler-sided end of the lever element opposite to the lever carrier.

In one variant a safety means can be provided to support the inhaler on at least one side in order to prevent the inhaler from twisting around a middle axis of the housing chamber relative to the connecting means. For proper operation of the inhaler it is necessary that the inhaler is reliably held by the connecting means. By twisting the inhaler relative to the connecting means there is a risk that the inhaler will drop out of the connecting means. This can, in particular, happen during a transport of the inhaler with the spacer chamber. With the aid of the safety means unintended twisting of the inhaler is avoided, as the inhaler is held in its position relative to the connecting means.

In one embodiment a supporting means can be provided on the inhaler-sided end of the lever element to support the inhaler on its rearward side facing away from the position of the lever element. It has been noted that when the lever element is operated, there is a risk that the inhaler and/or the container of the inhaler will bend backward, away from the spacer chamber, due to diagonally acting forces exerted by the lever element. Thus, the inhaler can be pressed out of the connecting means. To prevent this, the supporting means can be provided, with which the inhaler is supported rearward, i.e. on the side facing away from the spacer chamber. Thus, the inhaler is reliably held within the connecting means.

The safety means or the supporting means can each have a surface formed on the inhaler-sided end of the lever element. This means that the lever element is elongated at the inhaler-sided end, in order to provide the surfaces required for the previously described safety means and/or the supporting means. Another modification of the spacer chamber is not required, so that—as already mentioned above—also for the housing chamber a housing chamber can be used as it is known for spacer chambers from the prior art, on which a correspondingly formed lever element with various surfaces can be mounted.

The surface on the safety means and/or the corresponding surface on the supporting means serve to provide a stop for holding and/or supporting the inhaler. It can be designed as a part of the lever element, i.e. integrally connected with the lever element. For the design of the surface it suffices when it enables only a minor line or ring section-shaped contact with the inhaler.

In one embodiment a locking means can be provided to lock the position of the lever element in any one of the positions. As mentioned above, the lever element as a part of the operating means can be movable to at least two positions, namely to the first position in which the active surface acts, for example, presses, on the activation element of the inhaler as well as to the second position in which the active surface does not press on the activation element. In at least one of these positions the lever element can be locked in order to prevent unintended activation of the inhaler during the transport of the spacer chamber, for example.

Accordingly, the locking means can be movable between two states, namely a locking state and an operating state, with the locking means in the locking state serving to hold the lever element in a predetermined position and releasing a movement of the lever element in the operating state. Depending on the embodiment, the locking state can be the first or the second position of the lever element. This means that the lever element can also be locked in a position in which it presses on the activation element permanently. This is unproblematic, since the activation element causes a one-time emission of aerosol only when operated. If the activation element stays in the pressed position afterwards, no further aerosol is produced. Also no medical product or propellant gas can escape from the container of the inhaler.

The lever means can include a grip area to be gripped by an operator. In doing so, it is possible to change the position of the active area acting on the activation element relative to the grip area. The grip area can, for example, be the upper side of the lever element and pressed by the operator with his/her hand.

A change of the position of the active surface relative to the grip area can be practicable to adjust the device to inhalers of different sizes. For example, it is possible that the activation element comes to rest at various points and/or at different height levels, so that the distance between the active surface and the activation element varies. To adjust the device thereto, the position of the active surface can be changed, for example, by shifting or bolting down the element on which the active surface is provided. For this purpose, the lever element can, in particular, be divided into at least two parts whose distance to each other is adjustably variable.

The lever length can also be variable to adjust the device and, in particular, the operating means to various container sizes of the inhaler (length, height). Similarly, it is possible to provide different storage or mounting points of the lever element on the housing chamber and/or the lever carrier.

The connecting means can be held on a front side of the housing chamber and can be twistable on this front side to at least three positions, namely to a first rotational position in which the inhaler is held within the connecting means and the connecting means is held within the housing chamber, to a second rotational position in which the inhaler is removable from the connecting means and the connecting means is held within the housing chamber, and to a third rotational position in which the connecting means is removable from the front side of the housing chamber.

Thus, the inhaler is held within the connecting means in the first rotational position and insofar is ready for operation. The inhaler can be exchanged in the second rotational position without the connecting means being removable from the housing chamber. Rather, the connecting means continues to be held on the housing chamber. Only in the third rotational position, the connecting means can then be removed from the housing chamber, to obtain, for example, free access to the housing chamber for cleaning purposes. The various rotary positions can, e.g., be realized through bayonet catches, so that the connecting ring can be fastened on the housing chamber with the aid of a bayonet catch.

The thus described spacer chamber can especially be used in an inhalation device comprising an inhaler, with the inhaler including a container accommodating a medicinal product as well as a mouth element arranged on the container, and a dosage means functionally arranged between the container and the mouth element for producing an aerosol, with the aerosol containing a predetermined amount of the medicinal product. The inhaler can—with its mouth element—be fastened to the connecting means, with the activation element of the inhaler being a bottom area of the container.

Thus, the inhaler is a standard inhaler with which normally medicinal products for the treatment of respiratory diseases or similar are administered. Such an inhaler is also diversely known as an MDI (metered-dose inhaler).

Those skilled in the art will recognize additional features and advantages upon reading the following detailed description, and upon viewing the accompanying drawings.

BRIEF DESCRIPTION OF THE DRAWINGS

The elements of the drawings are not necessarily to scale relative to each other. Like reference numerals designate corresponding similar parts. The features of the various illustrated embodiments can be combined unless they exclude each other. Embodiments are depicted in the drawings and are detailed in the description which follows. In the drawings.

DETAILED DESCRIPTION

Figure 1:
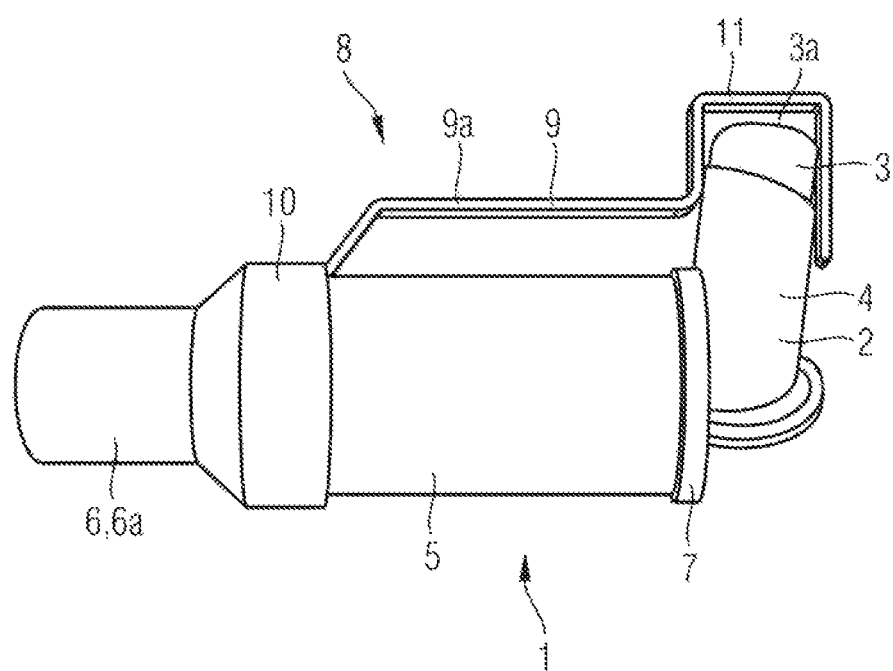
FIG. 1 shows an inhalation device comprising a spacer chamber and an inhaler in side view.

FIG. 1 shows an inhalation device comprising a spacer chamber 1 and an inhaler 2 in side view.

The inhaler 2 is a customary inhaler (also referred to as an MDI—metered-dose inhaler) with which a medicinal product in a predetermined dosage is converted into an aerosol, which can be inhaled by a patient via a mouthpiece not visible in FIG. 1. A container 3 containing the medicinal product and a propellant gas is inserted, in particular screwed, into a holder 4. Also the (non-visible) mouth element is designed integrally on the holder 4.

Since the structure of such an inhaler from the prior art is diversely known, any further explanation is unnecessary at this point.

By pressing the upper bottom 3a of the container 3 held with its outlet downward in the holder 4, a puff is activated and supplied to the mouth element (in FIG. 1 at the bottom left on the holder 4, however, not visible). To effect the puff, the patient must therefore press on the bottom 3a of the container 3 with some force.

The spacer chamber 1 includes a housing chamber 5, which essentially corresponds to a hollow cylindrical tube and is covered on the front sides. A mouthpiece 6 which, for example, can be provided with a check valve, is provided on a front side. The mouthpiece 6 is covered by a protective cover 6a in FIG. 1. On the opposite front-sided end of the housing chamber 5, a connecting means 7 is mounted, which, on one hand, closes the housing chamber 5 in a cover-like manner and, on the other hand, forms the connecting possibility to connect the inhaler 2.

An opening, which is not visible in FIG. 1, is formed in the connecting means 7, into which the mouth element of the inhaler 2 can be inserted. In that manner, the inhaler 2 is held safely on the housing chamber 5.

The structure of such a spacer chamber 1 is, for example, described in U.S. Pat. No. 7,562,656 B2. To avoid repetitions, reference is therefore made to that patent specification.

A lever means 8, which serves as an operating means, is mounted on the outside of the housing chamber 5. The lever means 8 includes a lever 9 serving as a lever element, which is held on the housing chamber 5 by a lever carrier 10.

The lever 9 is designed in such a manner that it extends from the lever carrier 10 arranged in the vicinity of the mouthpiece 6 along the middle axis of the housing chamber 5 rearwards in the direction of the inhaler 2 and there encloses the bottom 3a of the container 3 of the inhaler 2.

The lever 9 is movably held on the housing chamber 5 via the lever carrier 10, i.e. is movable and/or swivelable relative to the lever carrier 10. For this purpose, the lever 9 and the lever carrier 10 have a certain movability which enables, in particular, that the inhaler-sided end of the lever 9 can be moved in such a manner that an active surface 11 formed on the end can press on the bottom 3a of the container 3 to activate a puff. Thus, an operator of the inhalation device can hold the housing chamber 5 with the lever 9 with one hand and swivel the lever 9 in the direction of the housing chamber 5. In doing so, the operator can press on a grip area 9a of the lever 9. Thus, the active surface 11 is displaced and pressed against the bottom 3a of the inhaler container 3, whereby a puff can be activated. The aerosol from the container 3 enters the interior of the housing chamber 5 via the mouth element of the inhaler 2 and the connecting means 7, and can be inhaled there by the patient.

For the movability of the lever 9 it is above all essential that the active surface 11 can be moved in the direction of the bottom 3a. Accordingly, various solutions are possible for the design of the lever 9 and of the lever carrier 10 to achieve such movability.

For example, the lever carrier 10 can be elastic and hold the relatively rigid lever 9, which is then movable through its connection. Similarly, it is possible to design the lever carrier 10 rather rigid and to design the lever 9 as elastic. Due to the length of the lever 9, the desired movability of the active surface 11 provided on the inhaler-sided end can be achieved, despite the mouthpiece-side fixed end of the lever 9.

Similarly, it is possible that a hinge means is formed between the lever carrier 10 and the lever 9 to achieve the movability of the lever 9. The hinge means can be designed as a hinge with an additional axis element. Similarly, the hinge means can also be designed as a simple film hinge.

The lever carrier 10 can be firmly connected with the housing chamber 5. For example, it is possible to, e.g., shrink or glue the lever carrier 10 onto the outside of the housing chamber 5. Similarly, the lever carrier 10, which, for example, can be designed annular and thus encloses the housing chamber 5, can be designed in the form of a clamp which is screwed on the housing chamber 5.

In one variant the lever carrier 10 is merely clipped or pushed onto the housing chamber 5. The lever carrier 10 can also be slid into a pocket or a ring provided on the housing chamber 5.

No particular arrangements must be made on the outside of the housing chamber 5 in order to enable the mounting of the lever carrier 10. However, it is also possible to provide, for example, a circumferential groove on the housing chamber 5, in which the annular or clasp-shaped lever carrier 10 is held.

Further variants are described in the text below.

Figure 2A:
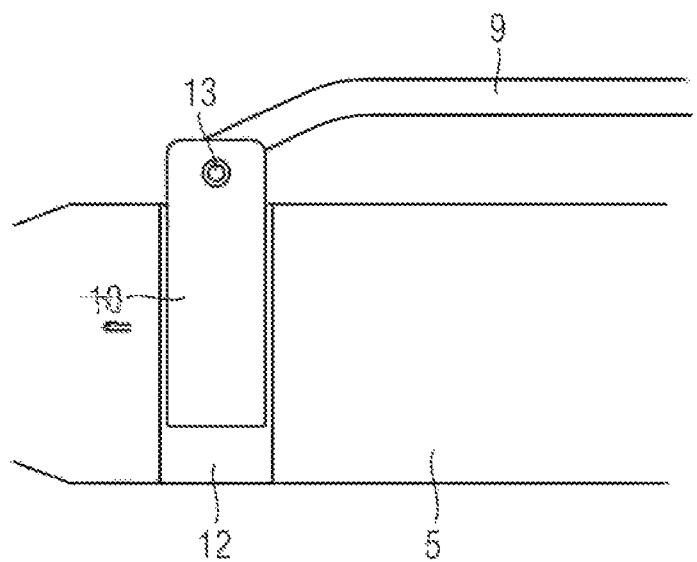
FIG. 2a shows a sectional view of an inhalation device in side view.
Figure 2B:
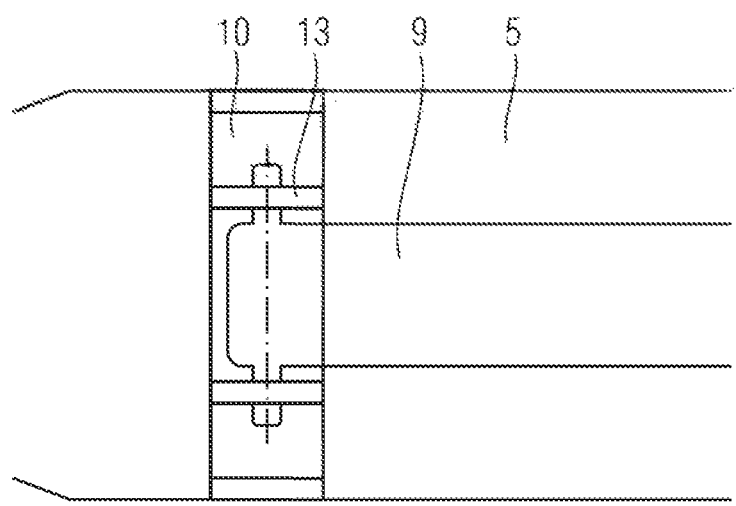
FIG. 2b shows the inhalation device of FIG. 2a in top view.

FIG. 2a shows a variant for the fastening of the lever 9 and/or of the lever carrier 10 in side view, and FIG. 2b shows the arrangement of FIG. 2a in top view.

A circumferential recess 12 in the form of a groove, a joint or of a cut-in, into which the lever carrier 10 is inserted, is provided in the outside wall of the housing chamber 5. The lever carrier 10 in the illustrated example is shown as an open clasp which is clipped into the recess 12. Alternatively, it would be possible to design the lever carrier 10 as a closed ring or as a clamp.

At the transition between the lever carrier 10 and the lever 9, a hinge means 13 is provided in the form of a swivel. With the aid of the hinge means 13 it is easily possible to swivel the lever 9 relative to the lever carrier 10 and the housing chamber 5.

Figure 3A:
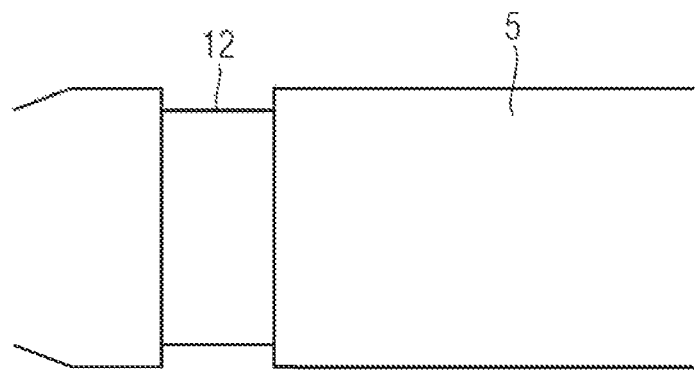
FIG. 3a shows a spacer chamber in side view.

In FIG. 3a the housing chamber 5 is shown with the recess 12, however, without the lever carrier 10.

Figure 3B:
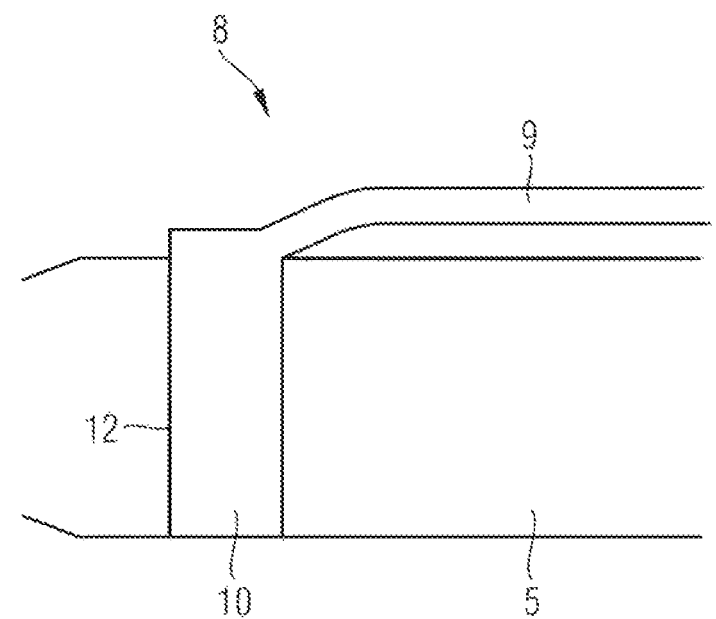
FIG. 3b shows a sectional view of the spacer chamber of FIG. 3a with a mounted lever means.

In FIG. 3b a simplified arrangement is shown where the lever carrier 10 is also inserted into the recess 12 in the form of a mounting clip. The lever 9 is connected with the lever carrier 10. Since the lever 9 has a certain degree of elasticity, in particular, spring elasticity, no additional hinge means is required to achieve movability of the lever 9.

In particular, the lever 9 and the lever carrier 10 can be manufactured integrally in the form of the entire lever means 8, for example, from plastic or from metal.

Figure 4:
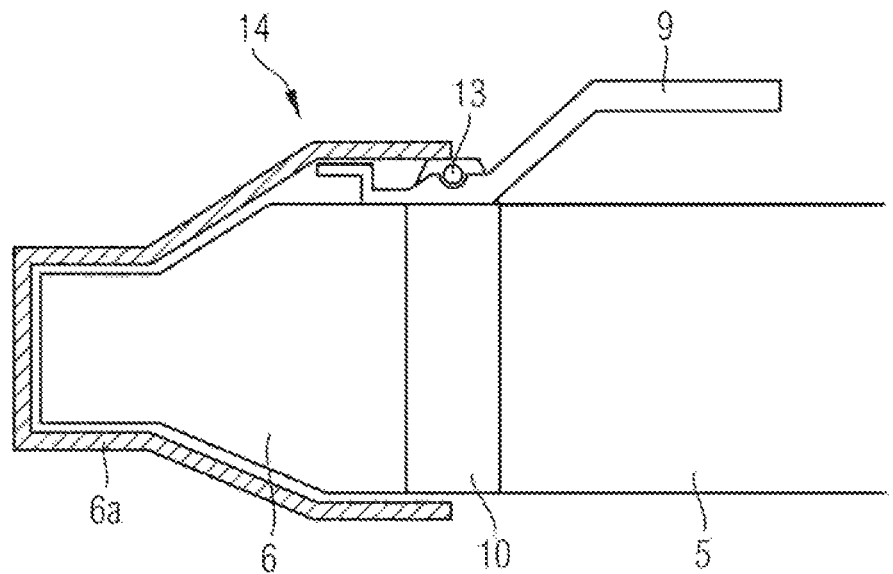
FIG. 4 shows a sectional view of a spacer chamber in side view.

FIG. 4 shows another variant where the lever carrier 10 and the lever 9 are designed rather rigid, and the lever 9 can be swiveled with respect to the lever carrier 10 due to the hinge means 13 arranged therebetween.

Furthermore, a transportation lock 14 is provided. The transportation lock 14 can be integrated into the protective cover 6a for the mouthpiece 6, i.e. be part of the protective cover 6a, or also be integrated into the mouthpiece 6. The effect of the transportation lock 14 is achieved in that the carrier 9 is extended beyond the hinge means 13 in the direction of the mouthpiece 6, and grips with this extension underneath the protective cover 6a and/or transportation lock 14. Therefore, if the protective cover 6a designed as a cap, for example, is mounted as shown in FIG. 4, the protective cover 6a as the transportation lock 14 overlaps the extended end of the lever 9 and blocks its movement.

Figure 5:
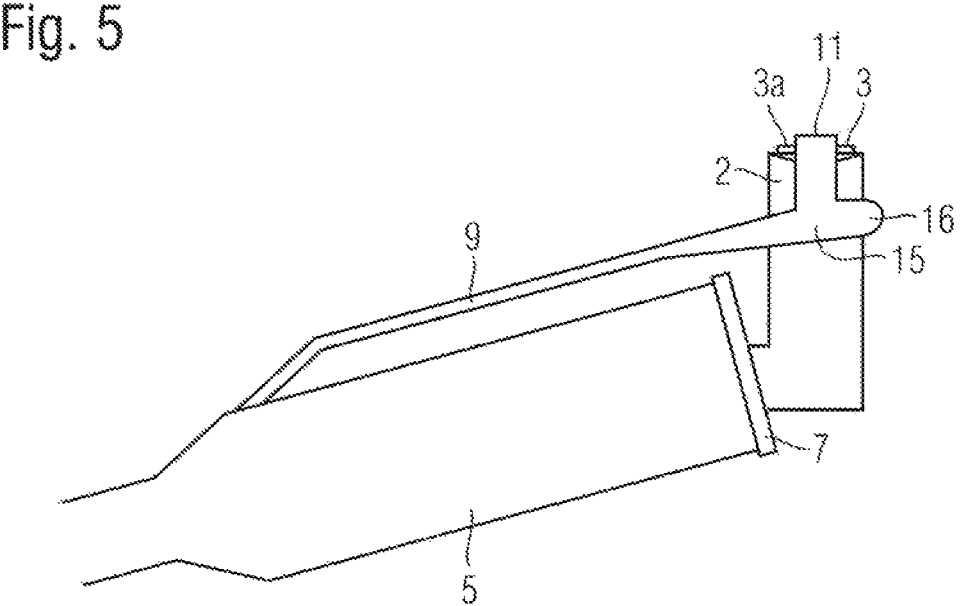
FIG. 5 shows a sectional view of an inhalation device in side view.

FIG. 5 shows another variant, where the design of the inhaler-sided end of the lever 9 is meant to be contemplated now.

As can be seen in FIG. 5, the active surface 11 is formed on a bracket which projects above the bottom 3a of the container 3. The lever 9 itself forms a lateral supporting surface 15 which serves as a safety means and supports the inhaler 2 in the operating position. Thus, it is prevented that the inhaler 2 can be twisted undesirably relative to the housing chamber 5. The inhaler 2 is held in the intended operating position through the design of the end of the lever 9.

The lateral supporting surface 15 turns into a rearward supporting surface 16 which serves as a supporting means. When operating the lever 9, a force is exerted on the inhaler 2 in the embodiment shown, as a result of which the inhaler 2 has the tendency to be pressed out of the connecting means 7. The rearward supporting surface 16 is provided to hold the inhaler 2 reliably within the connecting means 7. Thus, rearward evasion of the inhaler 2, away from the housing chamber 5 and the connecting means 7, is prevented. However, if no force is exerted on the inhaler 2 by the lever 9 which could press the inhaler 2 out of the connecting means 7, the supporting function of the supporting surface 16 is not required.

Figure 6:
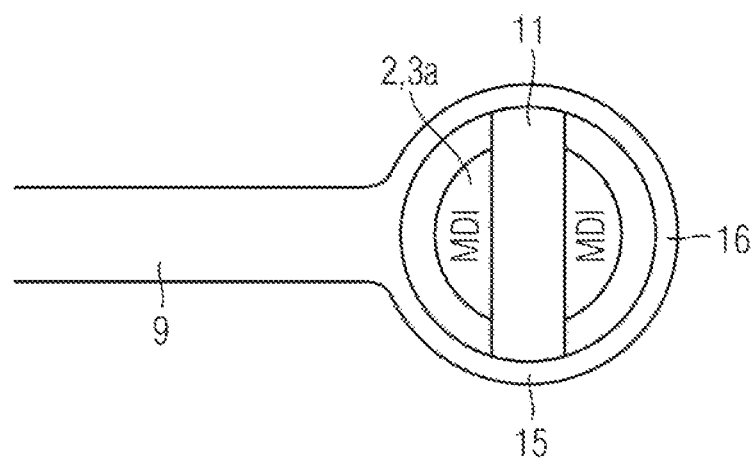
FIG. 6 shows a detailed view in top view.

FIG. 6 shows a variant of the inhaler-sided end of the lever 9 in top view.

In doing so, the lateral supporting surface 15 encloses the inhaler 2 in an annular manner. The bottom 3*a* of the inhaler 2 is covered by the arc-shaped active surface 11.

Figure 7:
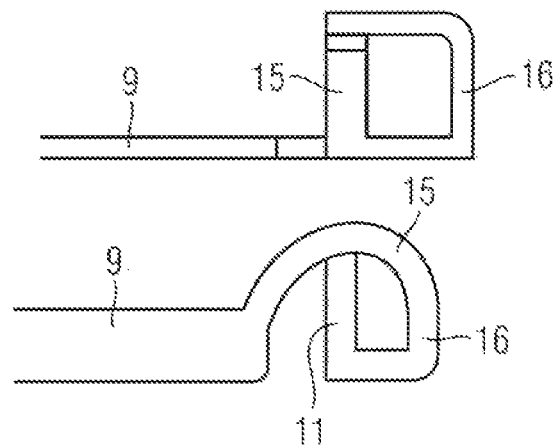
FIG. 7 shows variants of an inhaler-sided lever end.

FIG. 7 shows further variants for the design of the inhaler-sided end of the lever 9 in top and side view. Here the lateral supporting surface 15 encompasses the inhaler 2 only partly, and thus enables to swivel the inhaler 2 around the middle and/or longitudinal axis of the housing chamber 5.

The lateral supporting surface 15 can turn into the rearward supporting surface 16 in a transition-free manner, as, for example, as shown in FIGS. 6 and 7.

Figure 8:
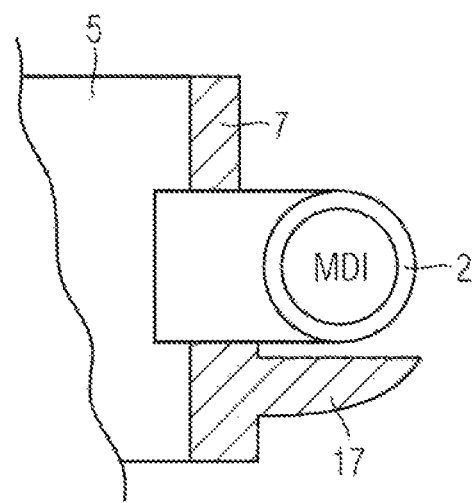
FIG. 8 shows a top view on an inhaler-sided end of a spacer chamber.

FIG. 8 shows a variant where a lateral supporting surface 17 is not formed on the end of the carrier 9, but on the connecting means 7. It can be seen from the illustration of FIG. 8 in top view that the inhaler 2 cannot be twisted at will relative to the housing chamber 5 and/or the connecting means 7, as it is held in a vertical position by the lateral supporting surface 17. Embodiments comprising two lateral supporting surfaces can also be advantageous.

Figure 9A:
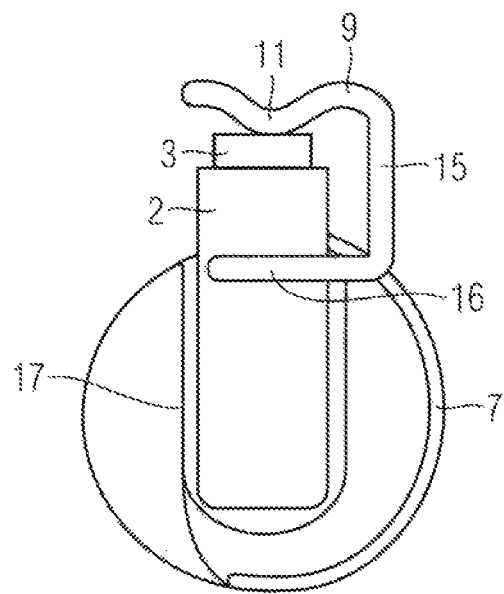
FIG. 9a shows a rear view of an inhalation device.
Figure 9B:
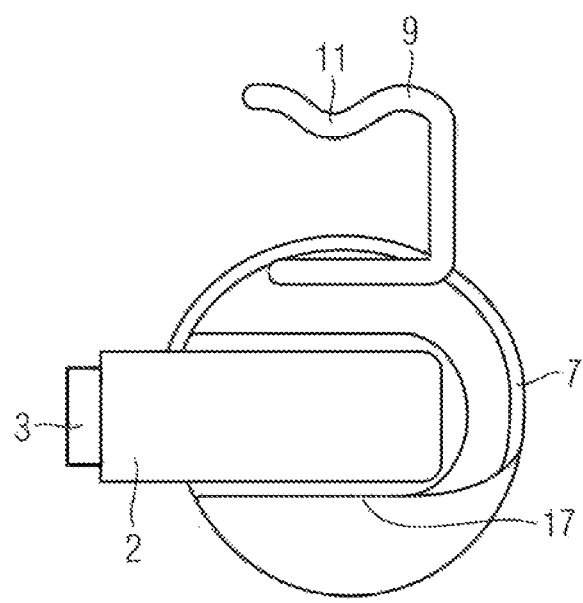
FIG. 9b shows the inhalation device of FIG. 9a with a twisted inhaler and a twisted connecting means.

FIG. 9*a* shows a perspective view of another variant in the operating position. FIG. 9*b* shows the variant in a position where the inhaler 2 can be removed.

The inhaler 2 is, similar to the variants shown in FIGS. 5 to 7, partly enclosed by the end of the carrier 9, so that the active surface 11 comes to rest opposite to the bottom 3*a* of the container 3, the lateral supporting surface 15 prevents twisting of the inhaler 2 in one direction, and the rearward supporting surface 16 blocks evasion of the inhaler 2 away from the housing chamber 5.

In addition, the lateral supporting surface 17 is provided on the annular connecting means 7, which blocks twisting of the inhaler 2 in a direction opposite to the lateral supporting surface 15.

The inhaler 2 can only be released through twisting together with the connecting means 7, as shown by FIG. 9*b*.

Additionally, it is possible to twist the connecting means 7 to a total of three positions, namely to the positions according to FIGS. 9*a* and 9*b* as well as to another position (based on FIG. 9*b* at 90° counterclockwise). In the latter position the connecting means can then be demounted from the housing chamber 5, to obtain, for example, free access to the housing chamber 5 for cleaning purposes. In doing so, it can be practical, if the connecting means 7 is fastened to the housing chamber 5 through a bayonet catch.

Figure 10:
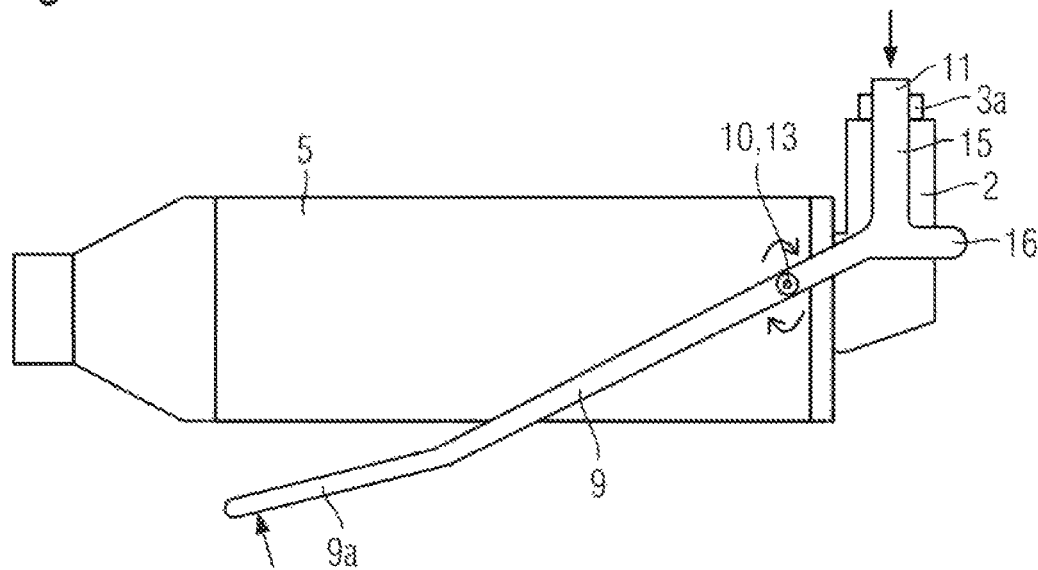
FIG. 10 shows a side view of a variant of an inhalation device.

FIG. 10 shows another variant where the lever carrier 10 is provided on the inhaler-sided end of the housing chamber 5. There also the hinge means 13 is arranged which enables swiveling of the lever 9 relative to the housing chamber 5.

In this case, the operator must press against the grip area 9*a* of the lever 9 (in the direction of the arrow)—in FIG. 10 from below—to activate a puff. By pressing the grip area 9*a* in the direction of the housing chamber 5, the opposite active surface 11 is lowered and operates the container bottom 3*a*.

Figure 11:
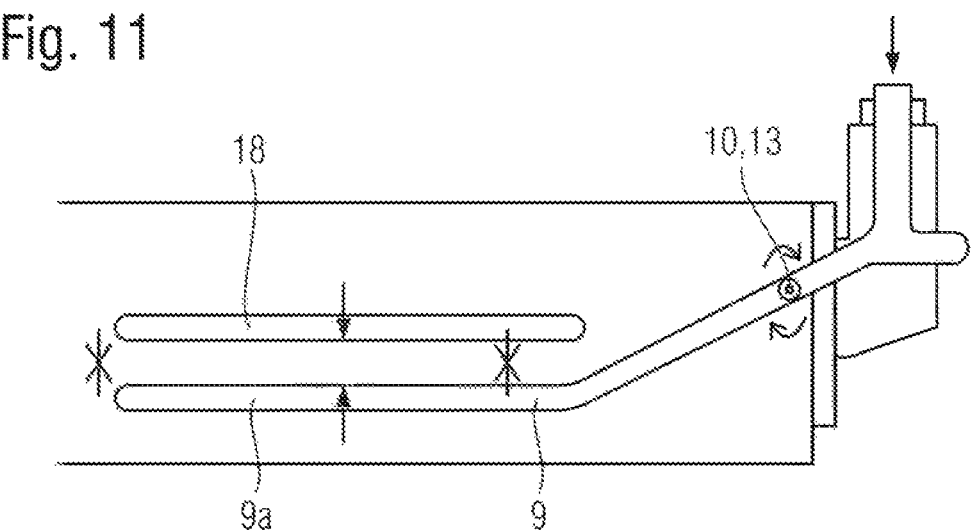
FIG. 11 shows another variant of an inhalation device in sectional view.

FIG. 11 shows another variant where, in addition to the lever 9, a grip 18 is provided on the housing chamber 5 to enable the operator to support his/her hand.

Figure 12:
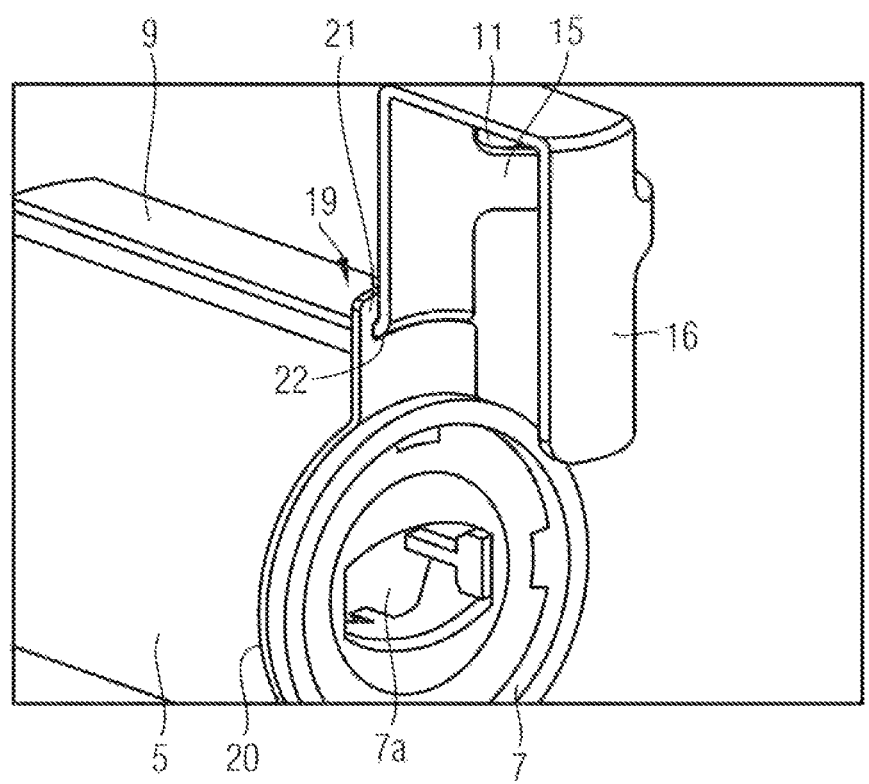
FIG. 12 shows a perspective sectional view of a spacer chamber comprising a locking means.

FIG. 12 shows an embodiment comprising a locking means 19.

When transporting the inhalation device there is a risk that, for example, pressure is accidently exerted on the lever 9 inside a handbag, and thus an unintended puff is activated. For this purpose, the locking means 19 is provided, which is to prevent unintended movement of the lever 9.

The locking means 19 includes a locking ring 20 with a locking extension 21 enclosing the housing chamber 5. A recess 22 is provided in the locking appendage 21, which can be guided to the position shown in FIG. 12 via the lever 9. Thus, the lever 9 is blocked in the position shown. In particular, the active surface 11 cannot press on the inhaler 2 (locking state).

To release the lever 9, the locking ring 20 is swiveled with the locking extension 21. Thus, the lever 9 glides from the recess 22 and is free to move (operating state).

In addition, the design of an annular connecting means 7 can be seen in FIG. 12, comprising an opening 7*a* into which a mouth element of the inhaler 2 can be inserted.

Figure 13:
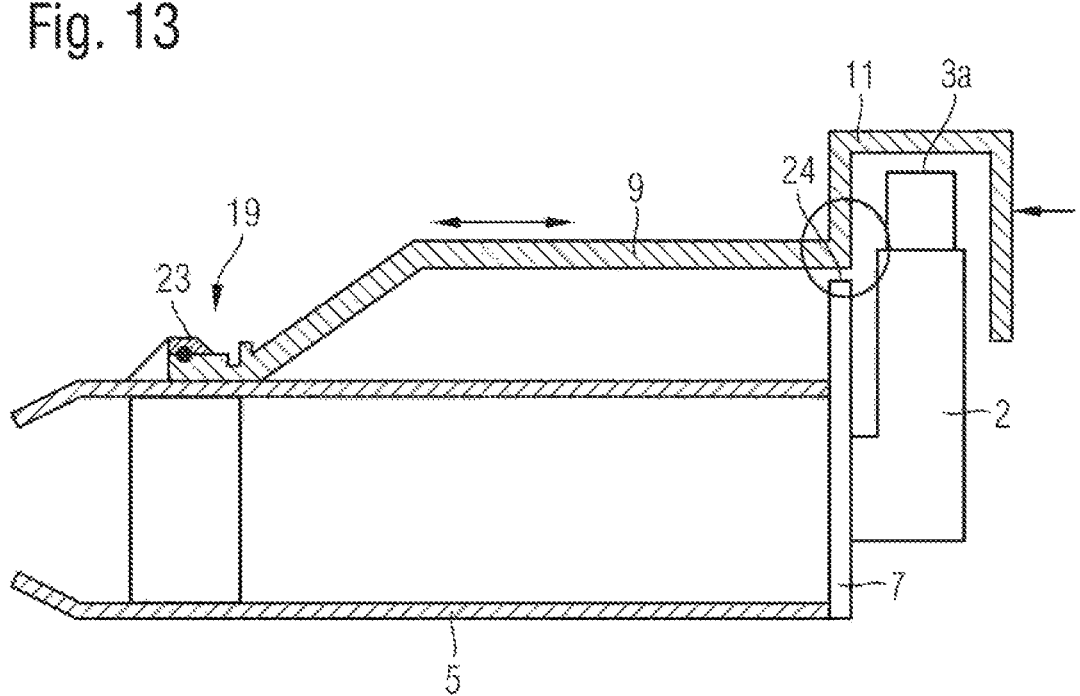
FIG. 13 shows a schematic sectional view of an inhalation device comprising a locking means.

FIG. 13 shows another example for a possible locking means 19. In the locking state illustrated in FIG. 13, the lever 9 is movable axially in two latching steps relative to the housing chamber 5. The latching steps are determined by a latching means 23. In the first latching step shown in FIG. 13, part of the lever 9 is located directly above a stop 24. Hence, the lever 9 can only minimally be moved downward in the direction of the inhaler 2. Thus, accidental activation of a puff is prevented.

When axially moving the lever 9 into the second latching step (in FIG. 13 to the left), the lever 9 is moved in such a manner that it cannot hit the stop 24 anymore. Thus, the lever 9 is freely movable downward, and the active surface 11 can press on the bottom 3*a* of the inhaler 2.

Figure 14:
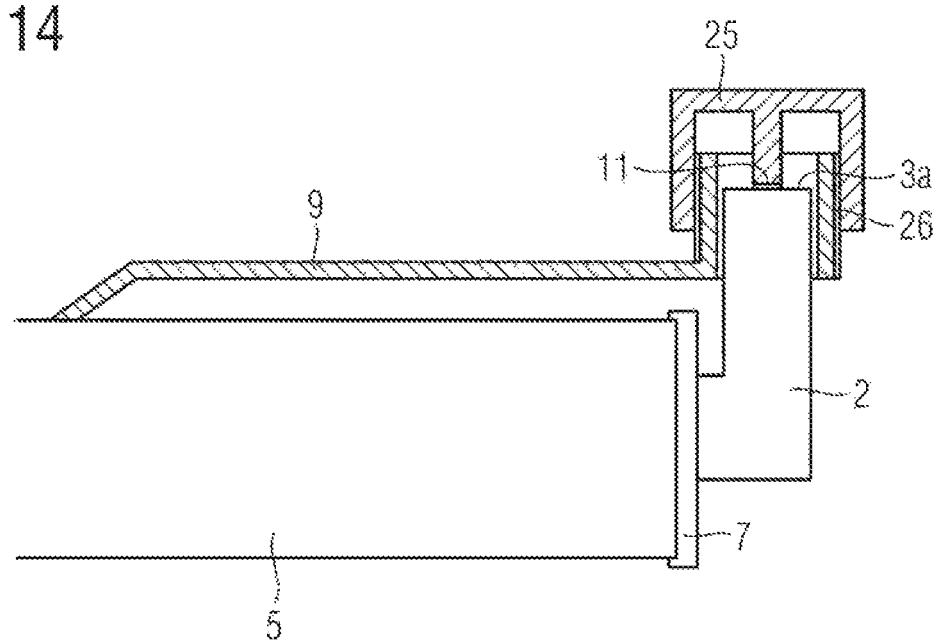
FIG. 14 shows a sectional view of an inhalation device for inhalers of various sizes.

FIG. 14 shows a variant where the inhalation device is adjustable to various sizes of inhalers 2.

For example, there are inhalers with different container sizes, with, in particular, the length, i.e. axial extension of the container 3 and thus the position of the container bottom 3*a* being variable.

In order to be able to adjust the lever 9 and the position of the active surface 11 to the different geometrical circumstances, the position of the active surface 11 is changeable relative to the remaining lever 9. This is achieved in the example shown in that the active surface 11 is designed on a cover 25 which is screwable relative to the lever 9. Depending on the axial position of the cover 25, the active surface 11 is at a different height with respect to the lever 9 and the inhaler 2.

Preferably, the position of the cover 25 can be fixed, for example, by a relatively tight-fitting thread 26 between the end of the lever 9 and the cover 25.

In one variant the cover 25 can also serve as a cap for the mouthpiece 6, if the spacer chamber is not used.

Alternatively, it is possible to lock the cover 25 in various axial positions.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

It is to be understood that the features of the various embodiments described herein may be combined with each other, unless specifically noted otherwise.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A spacer chamber for an inhaler, comprising:
a housing chamber;
a mouthpiece arranged on a first end of the housing chamber;
a connecting means arranged on a second end of the housing chamber and configured to connect to a mouthpiece of the inhaler, the mouthpiece of the inhaler being configured for insertion in an oral cavity of a patient and through which an aerosol is inhalable by the patient; and
an operating means held on the housing chamber which is movable to two positions and has an active surface that is arranged in such a manner that the active surface is configured to act on an activation element of the inhaler in any one of the two positions of the operating means, if the inhaler is connected to the connecting means, wherein:
the operating means includes a lever means;
the lever means includes a lever element and a lever carrier carrying the lever element;
the lever element is movable in a swivelable manner relative to the lever carrier; and
the lever carrier is fastened to the housing chamber adjacent to the mouthpiece of the housing chamber, so that the lever element extends away from the mouthpiece of the housing chamber along a middle axis of the housing chamber in a direction towards the second end of the housing chamber.

2. The spacer chamber of claim 1, wherein the lever carrier is fastened releasably on the housing chamber.

3. The spacer chamber of claim 1, further comprising a hinge means arranged between the lever element and the lever carrier, wherein the lever element is swivelable relative to the lever carrier due to the hinge means.

4. The spacer chamber of claim 1, wherein:
the lever element has an elongated extension and is held on the lever carrier on a carrier-sided end; and
the active surface is formed on an inhaler-sided end of the lever element opposite to the carrier sided end of the lever element.

5. The spacer chamber of claim 4, further comprising a supporting means provided on the inhaler-sided end of the lever element configured to support the inhaler at a rear side of the inhaler.

6. The spacer chamber of claim 5, wherein the supporting means has at least one surface formed on the inhaler-sided end of the lever element.

7. The spacer chamber of claim 1, further comprising a locking means for locking the operating means of the lever element in any one of the two positions.

8. The spacer chamber of claim 7, wherein the locking means is movable between a locking state and an operating state, wherein the locking means in the locking state is configured to hold the lever element in a predetermined position and release a movement of the lever element in the operating state.

9. The spacer chamber of claim 1, wherein:
the lever means includes a grip area configured to be gripped by an operator; and
a position of the active surface acting on the activation element relative to the grip area is changeable relative to the grip area.

10. The spacer chamber of claim 1, wherein the connecting means is held on the second end of the housing chamber and is twistable on the second end to at least three positions including:
a first rotational position configured such that the inhaler is held tightly within the connecting means and the connecting means is held tightly within the housing chamber;
a second rotational position configured such that the inhaler is removable from the connecting means and the connecting means is held tightly within the housing chamber; and
a third rotational position in which the connecting means is removable from the second end of the housing chamber.

11. The spacer chamber of claim 1, further comprising a safety means for supporting the inhaler on at least one side so as to prevent the inhaler from twisting around the middle axis of the housing chamber relative to the connecting means.

12. The spacer chamber of claim 11, wherein the safety means has at least one surface formed on an inhaler-sided end of the lever element.

13. The spacer chamber of claim 11, wherein the safety means has a surface formed on the connecting means.

14. An inhalation device comprising the spacer chamber of claim 1 and an inhaler, wherein:
the inhaler includes:
a container configured to accommodate a medicinal product, wherein the container is accommodated in a holder and a mouthpiece of the inhaler is arranged on the holder; and
a dosage means functionally arranged between the container and the mouthpiece arranged on the holder to produce an aerosol, the aerosol containing a predetermined amount of the medicinal product,
wherein the inhaler with the mouthpiece arranged on the holder is fastenable on the connecting means of the spacer chamber,
wherein an activation element of the inhaler is a bottom surface of the container.

* * * * *